US011373754B2

(12) United States Patent
Ogino (10) Patent No.: US 11,373,754 B2
(45) Date of Patent: Jun. 28, 2022

(54) ANESTHESIA MACHINE

(71) Applicant: Nihon Kohden Corporation, Tokyo (JP)

(72) Inventor: Yoshihiro Ogino, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 766 days.

(21) Appl. No.: 16/217,825

(22) Filed: Dec. 12, 2018

(65) Prior Publication Data

US 2019/0198165 A1    Jun. 27, 2019

(30) Foreign Application Priority Data

Dec. 25, 2017   (JP) .............................. JP2017-247876

(51) Int. Cl.
  *G06F 3/00* (2006.01)
  *G16H 40/63* (2018.01)
  *A61M 16/18* (2006.01)
  *G06F 3/048* (2013.01)

(52) U.S. Cl.
  CPC ............ *G16H 40/63* (2018.01); *A61M 16/18* (2013.01); *G06F 3/048* (2013.01); *A61M 2202/0241* (2013.01); *A61M 2202/048* (2013.01); *A61M 2205/502* (2013.01); *A61M 2205/505* (2013.01); *A61M 2205/80* (2013.01)

(58) Field of Classification Search
  CPC ...... G06F 3/048; G06F 3/0481; G06F 3/0482; G16H 40/63; A61M 16/18; A61M 5/145; A61M 5/14546; A61M 2202/048; A61M 2205/80; A61M 2205/502; A61M 2205/505
  See application file for complete search history.

(56) References Cited

U.S. PATENT DOCUMENTS

| 10,398,821 | B2 * | 9/2019 | Botterbusch | ........ A61M 60/268 |
| 2002/0038392 | A1 * | 3/2002 | De La Huerga | ....... G16H 20/17 710/8 |
| 2006/0081244 | A1 * | 4/2006 | Bouillon | ............... A61M 16/18 128/200.24 |
| 2008/0091083 | A1 * | 4/2008 | Yudkovitch | ............ G16H 20/10 600/300 |
| 2009/0288661 | A1 * | 11/2009 | Heinonen | ............. A61M 16/01 128/204.23 |

(Continued)

FOREIGN PATENT DOCUMENTS

| JP | 2013-218675 A | 10/2013 |
| JP | 2015-528711 A | 10/2015 |

(Continued)

OTHER PUBLICATIONS

Japanese Office Action dated Sep. 7, 2021 issued in Japanese Patent Application No. 2017-247876, 7 pages.

*Primary Examiner* — Cesar B Paula
*Assistant Examiner* — David Faber
(74) *Attorney, Agent, or Firm* — Pearne & Gordon LLP (57) ABSTRACT

A display device of an anesthesia machine which is communicable with at least one syringe pump that is an external apparatus displays an anesthesia information display screen. When a call switch is operated, a syringe pump information display screen indicating operation information of the syringe pump is displayed on the display device, in addition to the anesthesia information display screen.

14 Claims, 4 Drawing Sheets

(56) References Cited

U.S. PATENT DOCUMENTS

| | | | |
|---|---|---|---|
| 2009/0299156 A1* | 12/2009 | Simpson | A61M 5/1723 600/301 |
| 2010/0212668 A1* | 8/2010 | Flanagan | A61M 16/0833 128/203.16 |
| 2011/0000488 A1* | 1/2011 | Blomberg | A61M 16/18 128/203.14 |
| 2011/0155131 A1* | 6/2011 | Bottom | A61M 16/202 128/203.14 |
| 2013/0030290 A1 | 1/2013 | Nemoto | |
| 2014/0258918 A1 | 9/2014 | Morishima et al. | |
| 2015/0160845 A1 | 6/2015 | Lahtivuori et al. | |
| 2015/0177955 A1 | 6/2015 | Sunna | |
| 2015/0193585 A1 | 7/2015 | Sunna | |
| 2015/0199095 A1 | 7/2015 | Lahtivuori et al. | |
| 2016/0139787 A1* | 5/2016 | Joo | G06F 1/163 715/765 |
| 2016/0198099 A1* | 7/2016 | Han | H04N 21/4316 348/564 |
| 2017/0246378 A1 | 8/2017 | Nemoto | |
| 2017/0368293 A1 | 12/2017 | Nishiwaki et al. | |
| 2019/0099542 A1* | 4/2019 | Kuzelka | A61M 16/18 |
| 2019/0099581 A1* | 4/2019 | Kuzelka | A61M 16/024 |
| 2019/0151584 A1* | 5/2019 | Kuck | A61M 16/0066 |
| 2019/0227685 A1 | 7/2019 | Lahtivuori et al. | |
| 2020/0057552 A1 | 2/2020 | Sunna | |
| 2021/0124482 A1 | 4/2021 | Lindström | |

FOREIGN PATENT DOCUMENTS

| | | |
|---|---|---|
| JP | 2016-086972 A | 5/2016 |
| JP | 2016-131778 A | 7/2016 |
| WO | 2011/125987 A1 | 10/2011 |
| WO | 2016-117538 A1 | 7/2016 |

* cited by examiner

ANESTHESIA MACHINE

CROSS-REFERENCE TO RELATED APPLICATIONS

This application is based on and claims priority under 35 USC 119 from Japanese Patent Application No. 2017-247876 filed on Dec. 25, 2017, the contents of which are incorporated herein by reference.

TECHNICAL FIELD

The presently disclosed subject matter relates to an anesthesia machine. In the disclosure, "anesthesia machine" means an apparatus for administering inhalation anesthetic to a patient.

BACKGROUND ART

Patent Literature 1 discloses an example of such an anesthesia machine. The disclosed anesthesia machine includes a vaporizer. During surgery, for example, inhalation anesthetic is vaporized by the vaporizer, and then administered as an anesthetic gas to a patient.

Usually, an anesthesia machine includes a display device. The concentration of an anesthetic gas, vital signs information of a patient, and the like are displayed on the display device. The anesthesiologist manages the anesthetization of the patient while referring information displayed on the display device.

CITATION LIST

Patent Literature

Patent Literature 1: JP-A-2016-131778

SUMMARY OF INVENTION

During surgery, there is a case where anesthetic management and infusion management are performed by using an external apparatus such as a syringe pump in addition to the above-described anesthesia machine. A syringe pump is an apparatus for administrating a predetermined amount of medical solutions into the body of a patient through a syringe (for example, intravenous injection). Such medical solutions include intravenous anesthetic.

Also such an external apparatus usually includes a display device. The administered amounts of the medical solutions and the vital signs information of the patient are displayed on the display device. The anesthesiologist manages infusion administered to the patient while referring information displayed on the display device.

In the case where an anesthesia machine and an external apparatus are used together, the apparatuses are usually disposed in different separated places. Therefore, the anesthesiologist must manage the condition of the patient while moving between the apparatuses.

It is an object of the presently disclosed subject matter to reduce the burden of an anesthesiologist in the case where an anesthesia machine and an external apparatus are used together.

In order to achieve the above object, a mode of the presently disclosed subject matter is an anesthesia machine including a communicating section which is communicable with at least one external apparatus;

a display device which displays a first screen indicating anesthesia information; and a first operation receiving section which receives a first input operation, wherein when the first operation receiving section receives the first input operation, a second screen indicating operation information of the external apparatus is displayed on the display device, in addition to the first screen.

According to the configuration, in the case where the anesthesia machine and an external apparatus are used together, while performing anesthetic management of a patient through the display device of the anesthesia machine, an anesthesiologist is enabled to check the operation state of the external apparatus, by performing as necessary a first input operation on the first operation receiving section. That is, the anesthesiologist is not required to move to a place where the external apparatus is disposed, in order to check the operation state of the external apparatus during the anesthetic management using the anesthesia machine. Therefore, the burden of the anesthesiologist can be reduced. Moreover, the necessity of considering the movement line of the anesthesiologist is reduced, and hence the degree of freedom of the place where the external apparatus is disposed is enhanced.

The second screen is not always displayed on the display device of the anesthesia machine, but displayed only in the case where the first operation receiving section receives the first input operation. Therefore, the display of the second screen does not disturb the anesthetic management performed through the first screen. Also in this point, the burden of the anesthesiologist can be reduced in the case where the anesthesia machine and the external apparatus are used together.

DESCRIPTION OF EMBODIMENTS

Figure 1:
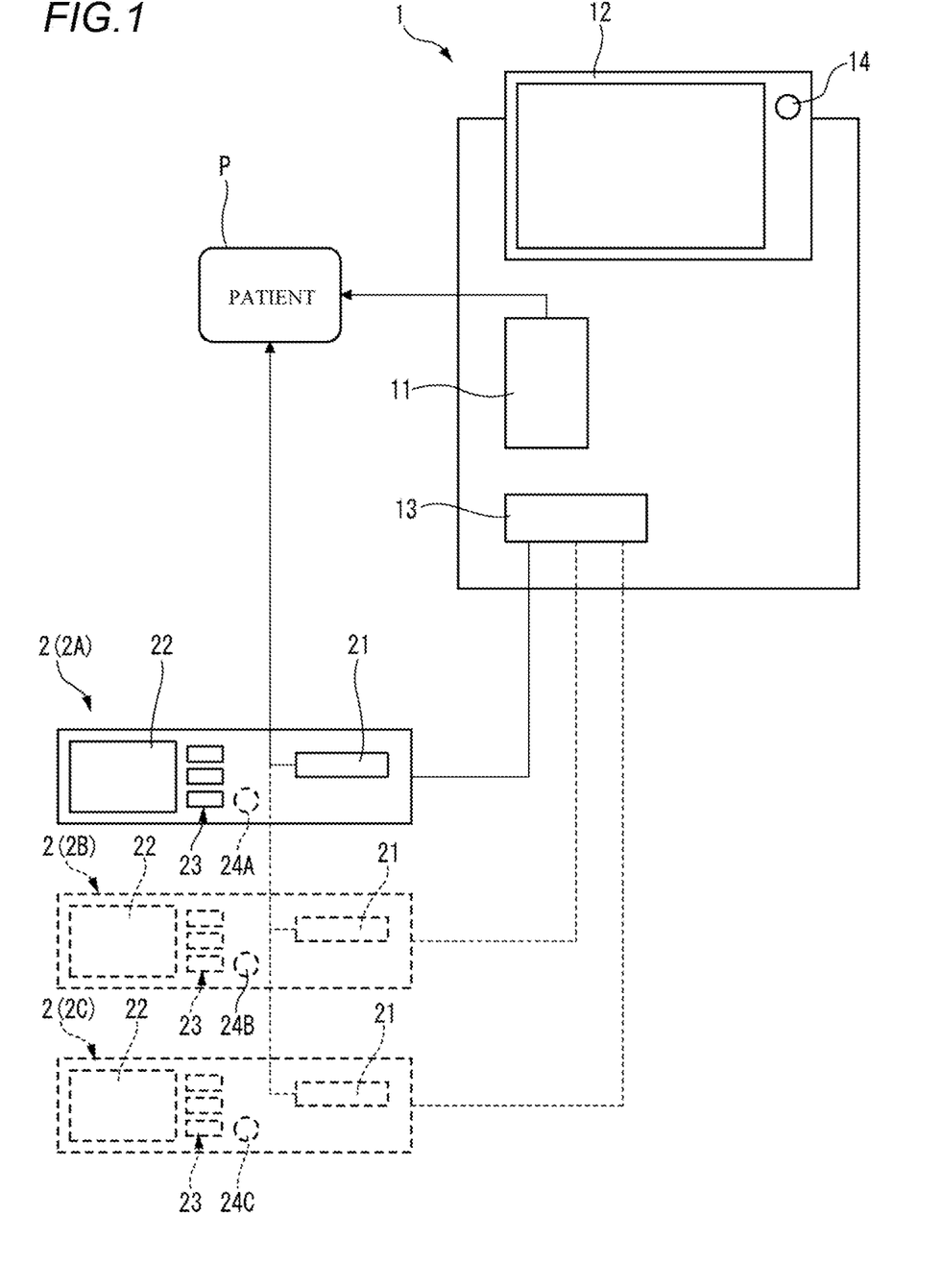
FIG. 1 diagrammatically illustrates the configuration of an anesthesia machine of an embodiment.

An embodiment will be described in detail with reference to the accompanying drawings. FIG. 1 diagrammatically illustrates the configuration of an anesthesia machine 1 of the embodiment.

The anesthesia machine 1 is an apparatus for administrating inhalation anesthetic to a patient P. The anesthesia machine 1 may include a vaporizer 11. In the case where the inhalation anesthetic is liquid at normal temperature, the inhalation anesthetic is vaporized by the vaporizer 11, and then administered as an anesthetic gas to the patient P.

Figure 2A:
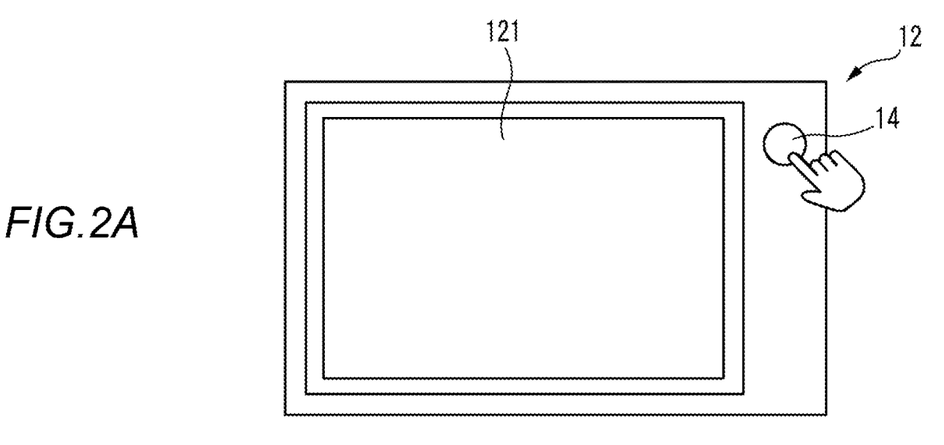
FIGS. 2A to 2C illustrate an example of the state transition of a display device in the anesthesia machine.

The anesthesia machine 1 may include a display device 12. As illustrated in FIG. 2A, the display device 12 is a device for displaying an anesthesia information display screen 121.

Numerical information indicating the concentration and administered amount of the inhalation anesthetic, a trend graph indicating temporal changes of the concentration and administered amount of the inhalation anesthetic, numerical information indicating the vital signs information of the patient P, and the like may be displayed on the anesthesia information display screen 121. Examples of the vital signs information are the heart rate, the blood pressure, the arterial oxygen saturation, and the like. The anesthesia information display screen 121 may include a display region for notifying of an abnormality in at least one of the patient P and the anesthesia machine 1. The anesthesiologist manages the anesthetization of the patient while referring to the anesthesia information display screen 121. The anesthesia information display screen 121 is an example of the first screen.

As illustrated in FIG. 1, the anesthesia machine 1 may include a communicating section 13. The communicating section 13 may include an interface which enables communication with at least one syringe pump 2 to be performed.

The syringe pump 2 is an apparatus for administrating a predetermined amount of medical solutions into the body of the patient P through a syringe (for example, intravenous injection). The syringe pump 2 is an example of the external apparatus. The syringe pump 2 may include the syringe 21. The amount of medical solutions suppled to the patient P is adjusted by an operation in which the syringe 21 is driven by a driving apparatus that is not shown.

The communication between the syringe pump 2 and the communicating section 13 may be performed in a wired manner, or in a wireless manner. The connection between the syringe pump 2 and the communicating section 13 may be established directly or indirectly through at least one relay unit.

The syringe pump 2 may include a display device 22. The display device 22 is a device for displaying an operation information display screen on which operation information of the syringe pump 2 is displayed. Numerical information indicating the rate, amount, and accumulated amount of administration of the medical solutions, and the like may be displayed on the operation information display screen. The operation information display screen may include also a display region for notifying of an abnormality in at least one of the syringe pump 2 and the patient P. The anesthesiologist may manage the infusion administration to the patient P while referring to the information displayed on the display device 22.

The anesthesia machine 1 may include a call switch 14. The call switch 14 is a hardware switch which receives a press operation. When the call switch 14 is pressed under conditions that the anesthesia information display screen 121 is displayed on the display device 12, as illustrated in FIG. 2A, a syringe pump information display screen 122 is displayed in addition to the anesthesia information display screen 121, on the display device 12. The call switch 14 is an example of the first operation receiving section. A press operation performed on the call switch 14 is an example of the first input operation.

The syringe pump information display screen 122 contains at least part of information contained in an operation displaying screen which is displayed on the display device 22 of the syringe pump 2. Namely, the syringe pump information display screen 122 indicates operation information of the syringe pump 2. The syringe pump information display screen 122 is an example of the second screen.

Specifically, the anesthesia machine 1 acquires data corresponding to information which is displayed on the operation displaying screen of the syringe pump 2, from the syringe pump 2 through the communicating section 13. The data are processed by a processor or the like which is not shown, and then visualized on the syringe pump information display screen 122.

According to the configuration, in the case where the anesthesia machine 1 and the syringe pump 2 are used together, while performing anesthetic management of the patient P through the display device 12 of the anesthesia machine 1, the anesthesiologist is enabled to check the operation state of the syringe pump 2, by operating as necessary the call switch 14. That is, the anesthesiologist is not required to move to a place where the display device 22 is disposed, in order to check the operation state of the syringe pump 2 during the anesthetic management using the anesthesia machine 1. Therefore, the burden of the anesthesiologist can be reduced. Moreover, the necessity of considering the movement line of the anesthesiologist is reduced, and hence the degree of freedom of the place where the syringe pump 2 is disposed is enhanced.

The syringe pump information display screen 122 is not always displayed on the display device 12 of the anesthesia machine 1, but displayed only in response to an operation performed on the call switch 14. Therefore, the display of the syringe pump information display screen 122 does not disturb the anesthetic management performed through the anesthesia information display screen 121. Also in this point, the burden of the anesthesiologist can be reduced in the case where the anesthesia machine 1 and the syringe pump 2 are used together.

In the case where the display device 12 includes a touch panel, the call switch 14 may be provided in the form of a switch image which is displayed on the display device 12, and which can be operated by a touch. In this case, the switch image is another example of the first operation receiving section, and the touch operation performed on the switch image is another example of the first input operation. The display of the syringe pump information display screen 122 may be performed in response to a voice input of a predetermined first phrase. In this case, a configuration which receives the voice input is a further example of the first operation receiving section, and the voice input of the first phrase is a further example of the first input operation.

Figure 2B:
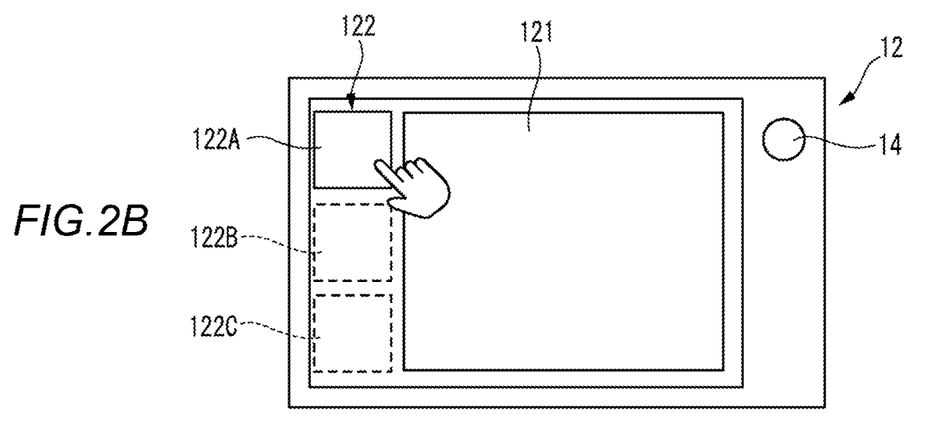

The syringe pump information display screen 122 may be displayed superimposed on the anesthesia information display screen 121. In the embodiment, however, the syringe pump information display screen 122 is displayed without superimposed on the anesthesia information display screen 121, as illustrated in FIG. 2B. At this time, the size of the anesthesia information display screen 121 is reduced as compared with the size at which the screen is displayed before the syringe pump information display screen 122 is displayed.

According to the configuration, the display of the syringe pump information display screen 122 does not disturb the viewing of the anesthesia information display screen 121, and both anesthetic management and infusion management can be efficiently performed.

Preferably, the size of the syringe pump information display screen 122 may be smaller than that of the anesthesia information display screen 121 which is reduced in size.

In the anesthesia information display screen 121 which is reduced in size, preferably, the time axis of the trend graph is shortened while maintaining the display of numerical information.

As illustrated in FIG. 1, the syringe pump 2 may include an operation receiving section 23. The operation receiving section 23 is configured by a switch group for controlling the operation of the syringe pump 2. Examples of the operation of the syringe pump 2 which is controlled by the switch group are the starting and ending of the infusion administration, and the rising and lowering of the rate of the infusion administration. At least one of switches constituting the switch group may be a hardware switch, or a switch image which is displayed on the display device 12, and which can be operated by a touch.

Figure 2C:
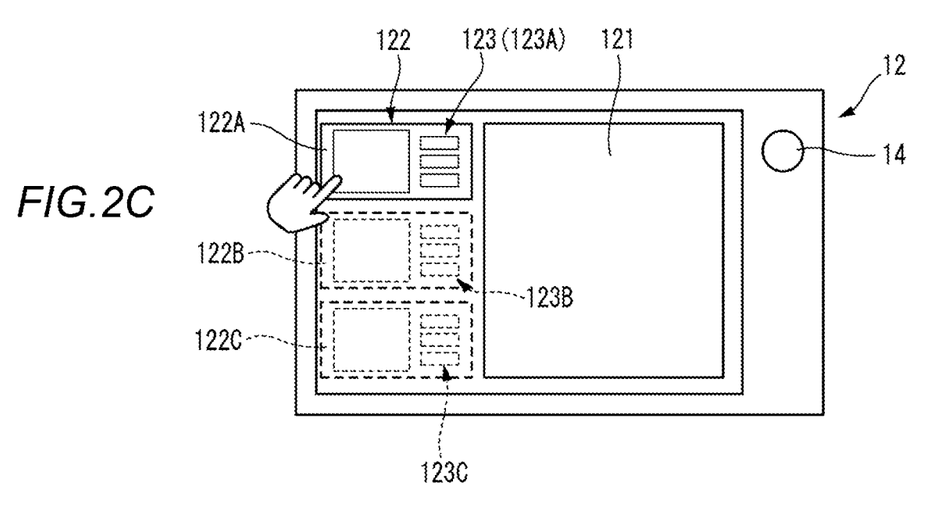

When a part of the syringe pump information display screen 122 is touch operated in the state where the syringe pump information display screen 122 is displayed on the display device 12 as illustrated in FIG. 2B, the syringe pump information display screen 122 is expanded as illustrated in FIG. 2C. A part of the syringe pump information display screen 122 is an example of the second operation receiving section, and the touch operation is an example of the second input operation. The size of the syringe pump information display screen 122 which is illustrated in FIG. 2B is an example of the first size, and that of the syringe pump information display screen 122 which is illustrated in FIG. 2C is an example of the second size.

A remote operation receiving section 123 is placed in the expanded syringe pump information display screen 122. The remote operation receiving section 123 may include a plurality of switch images which can be touch operated. The switch images are associated with the switches disposed in the operation receiving section 23 of the syringe pump 2, respectively. Namely, the remote operation receiving section 123 receives an operation of remotely controlling the syringe pump 2.

An operation which is input through the remote operation receiving section 123 is converted into a corresponded signal by a processor or the like which is not shown, and then transmitted to the syringe pump 2 through the communicating section 13. The signal is treated as equivalent to a signal which is input through the operation receiving section 23. The syringe pump 2 which receives the transmitted signal executes an operation corresponding to the signal.

According to the configuration, in the case where the anesthesia machine 1 and the syringe pump 2 are used together, while performing anesthetic management of the patient P through the display device 12 of the anesthesia machine 1, the anesthesiologist is enabled to remotely control the operation of the syringe pump 2, by operating as necessary the remote operation receiving section 123. That is, the anesthesiologist is not required to move to a place where the operation receiving section 23 is disposed, in order to operate the syringe pump 2 during the anesthetic management using the anesthesia machine 1.

The remote operation receiving section 123 is not always displayed on the display device 12 of the anesthesia machine 1, but displayed only in response to a predetermined operation (the second input operation) performed after the syringe pump information display screen 122 is called up. When it is requested only to check the operation state of the syringe pump 2, the syringe pump information display screen 122 is set to remain in the reduced size. Therefore, the display of the remote operation receiving section 123 does not disturb the anesthetic management performed through the anesthesia information display screen 121. Also in this point, the burden of the anesthesiologist can be reduced in the case where the anesthesia machine 1 and the syringe pump 2 are used together.

The anesthesia machine 1 may be configured so that, when an operation through the remote operation receiving section 123 of the anesthesia machine, and that through the operation receiving section 23 of the syringe pump 2 are simultaneously performed, the operation through the operation receiving section 23 has a priority.

The size (the second size) of the syringe pump information display screen 122 which is expanded as illustrated in FIG. 2C may be identical with that of an operation information display screen which is displayed on the display device 22 of the syringe pump 2 illustrated in FIG. 1. The information layout in the expanded syringe pump information display screen 122 may be identical with that in the operation information display screen of the syringe pump 2.

According to the configuration, in the case where the syringe pump 2 is remotely controlled from the anesthesia machine 1, the anesthesiologist can be provided, on the display device 12, with an operation sensing which is identical with that in the case where the operation is controlled through the operation information display screen displayed on the display device 22. Therefore, it is possible to reduce the burden of the anesthesiologist in the case where the syringe pump 2 is remotely controlled while anesthetic management is performed through the anesthesia machine 1.

Based on this point of view, it is preferable that the layout of the remote operation receiving section 123 which is paced in the expanded syringe pump information display screen 122 may be identical with that of the operation receiving section 23 of the syringe pump 2 which is remotely controlled.

As described above, the syringe pump information display screen 122 having the size (the first size) which is illustrated in FIG. 2B functions also as a receiving section for a touch operation (the second input operation) of expanding the syringe pump information display screen 122.

According to the configuration, the anesthesiologist can be provided with a user interface which involves an operation sensing that is more intuitive. In the below-described case where the anesthesia machine 1 remotely controls a plurality of syringe pumps, particularly, it is possible to intuitively know which one of the syringe pumps is the operation object.

Alternatively, the operation of expanding the syringe pump information display screen 122 may be input through a hardware switch which is disposed in the vicinity of the display device 12. In the alternative, the hardware switch is another example of the second operation receiving section, and an operation of pressing the hardware switch is another example of the second input operation. The syringe pump information display screen 122 may be expanded in response to a voice input of a predetermined second phrase. In this case, a configuration which receives the voice input is a further example of the second operation receiving section, and the voice input of the second phrase is a further example of the second input operation.

The expanded syringe pump information display screen 122 may be displayed superimposed on the anesthesia information display screen 121. In the embodiment, however, the expanded syringe pump information display screen 122 is displayed without superimposed on the anesthesia information display screen 121, as illustrated in FIG. 2C. At this time, the size of the anesthesia information display screen 121 is reduced as compared with the size at which the screen is displayed before the syringe pump information display screen 122 is expanded.

According to the configuration, the expanding of the syringe pump information display screen 122 does not disturb the viewing of the anesthesia information display screen 121, and both anesthetic management and infusion management can be efficiently performed.

Preferably, the size of the expanded syringe pump information display screen 122 may be smaller than that of the anesthesia information display screen 121 which is further reduced in size.

In the anesthesia information display screen 121 which is further reduced in size, preferably, the time axis of the trend graph is shortened while maintaining the display of numerical information.

As illustrated in FIG. 2C, when a part of the syringe pump information display screen 122 is touch operated in the state where the syringe pump information display screen 122 is enlarged and displayed on the display device 12, the syringe pump information display screen 122 returns to its original size as illustrated in FIG. 2B. A part of the expanded syringe pump information display screen 122 is an example of the third operation receiving section, and the touch operation is an example of the third input operation.

In the case where a time period when an input operation is not performed on the remote operation receiving section 123 reaches a predetermined value, alternatively, the remote operation receiving section 123 automatically returns to its original size.

According to the configuration, the time period when the display device 12 is occupied by the remote operation receiving section 123 can be shortened to the minimum necessary. Moreover, it is possible to suppress the possibility that an accidental input operation is performed on the remote operation receiving section 123.

As described above, the expanded syringe pump information display screen 122 illustrated in FIG. 2C functions also as a receiving section for a touch operation (the third input operation) of returning the size of the syringe pump information display screen 122 to the original size.

According to the configuration, the anesthesiologist can be provided with a user interface which involves an operation sensing that is more intuitive. In the below-described case where the anesthesia machine 1 remotely controls the plurality of syringe pumps, particularly, it is possible to intuitively know which one of the syringe pumps is the operation object.

Alternatively, the operation of returning the size of the syringe pump information display screen 122 to the original size may be input through a hardware switch which is disposed in the vicinity of the display device 12. In the alternative, the hardware switch is another example of the third operation receiving section, and an operation of pressing the hardware switch is another example of the third input operation. The syringe pump information display screen 122 may be downsized in response to a voice input of a predetermined third phrase. In this case, a configuration which receives the voice input is a further example of the third operation receiving section, and the voice input of the third phrase is a further example of the third input operation.

As indicated by the broken lines in FIG. 1, the anesthesia machine 1 may be communicable with a plurality of syringe pumps 2. In the example, the anesthesia machine is communicable with three syringe pumps, i.e., a first syringe pump 2A, a second syringe pump 2B, and a third syringe pump 2C. In the case where the syringe pump 2 is used as an administration apparatus for administrating intravenous anesthetic, a plurality of syringe pumps 2 are usually used. For example, the first syringe pump 2A may be used for administrating a sedative, the second syringe pump 2B may be used for administrating an analgesic, and the third syringe pump 2C may be used for administrating a muscle relaxant.

Usually, the plurality of syringe pumps 2 are supported by a rack so as to be vertically arranged. In the example, the first syringe pump 2A is placed above the second syringe pump 2B, and the second syringe pump 2B is placed above the third syringe pump 2C.

According to the configuration, as illustrated in FIG. 2B, the syringe pump information display screen 122 which is displayed in response to an operation performed on the call switch 14 may include a first region 122A, a second region 122B, and a third region 122C.

The first region 122A may include at least part of information contained in the operation displaying screen which is displayed in the display device 22 of the first syringe pump 2A. That is, the first region 122A indicates the operation information of the first syringe pump 2A.

The second region 122B may include at least part of information contained in the operation displaying screen which is displayed in the display device 22 of the second syringe pump 2B. That is, the second region 122B indicates the operation information of the second syringe pump 2B.

The third region 122C may include at least part of information contained in the operation displaying screen which is displayed in the display device 22 of the third syringe pump 2C. That is, the third region 122C indicates the operation information of the third syringe pump 2C.

Specifically, the anesthesia machine 1 acquires data corresponding to information which is displayed on the operation displaying screen of the first syringe pump 2A, from the first syringe pump 2A through the communicating section 13. The data are processed by the processor or the like which is not shown, and then visualized on the first region 122A.

In the same or similar manner, the anesthesia machine 1 acquires data corresponding to information which is displayed on the operation displaying screen of the second syringe pump 2B, from the second syringe pump 2B through the communicating section 13. The data are processed by the processor or the like which is not shown, and then visualized on the second region 122B.

In the same or similar manner, the anesthesia machine 1 acquires data corresponding to information which is displayed on the operation displaying screen of the third syringe pump 2C, from the third syringe pump 2C through the communicating section 13. The data are processed by the processor or the like which is not shown, and then visualized on the third region 122C.

In the syringe pump information display screen 122, the first region 122A is placed above the second region 122B, and the second region 122B is placed above the third region 122C. That is, the arrangement sequence of the first syringe pump 2A, the second syringe pump 2B, and the third syringe pump 2C is reflected in that of the first region 122A, the second region 122B, and the third region 122C in the syringe pump information display screen 122.

According to the configuration, in the case where the anesthesia machine 1 and the plurality of syringe pumps 2 are used together, the status of the work of checking the display devices 22 of the plurality of syringe pumps 2 can be reproduced on the display device 12 of the anesthesia machine 1 without causing a feeling of strangeness. Therefore, the burden of the anesthesiologist can be reduced.

As illustrated in FIG. 2B, when one of the first region 122A, the second region 122B, and the third region 122C is touch operated in the state where the syringe pump information display screen 122 is displayed on the display device 12, the syringe pump information display screen 122 is expanded as illustrated in FIG. 2C.

In the expanded syringe pump information display screen 122, also each of the first region 122A, the second region 122B, and the third region 122C is expanded. The expanded first region 122A may include a first remote operation receiving section 123A. The first remote operation receiving section 123A receives an operation of remotely controlling the first syringe pump 2A. The expanded second region 122B may include a second remote operation receiving section 123B. The second remote operation receiving section 123B receives an operation of remotely controlling the second syringe pump 2B. The expanded third region 122C may include a third remote operation receiving section 123C. The third remote operation receiving section 123C receives an operation of remotely controlling the third syringe pump 2C.

Figure 3A:
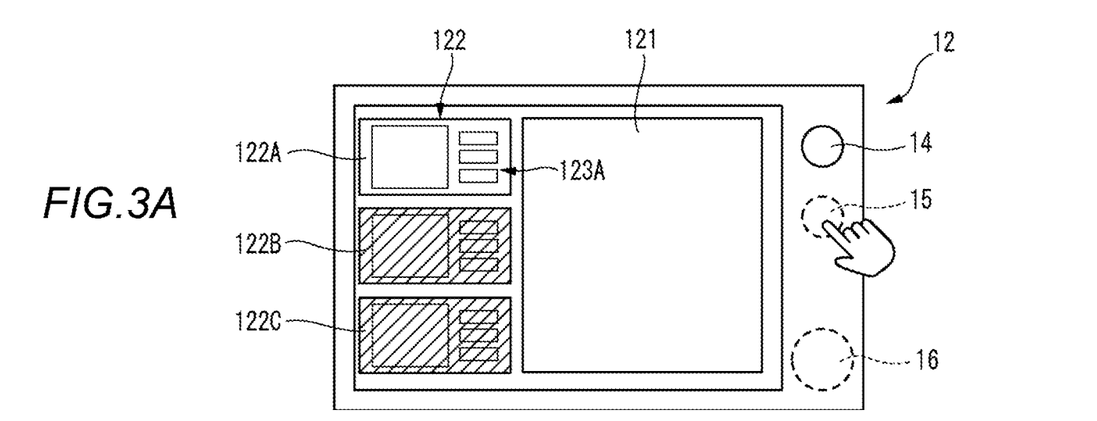
FIGS. 3A to 3C illustrate another example of the state transition of the display device.
Figure 3B:
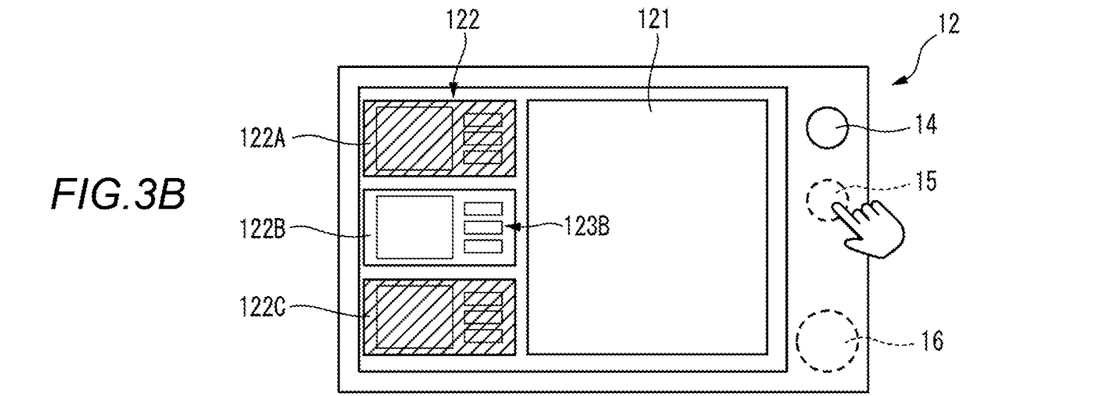
Figure 3C:
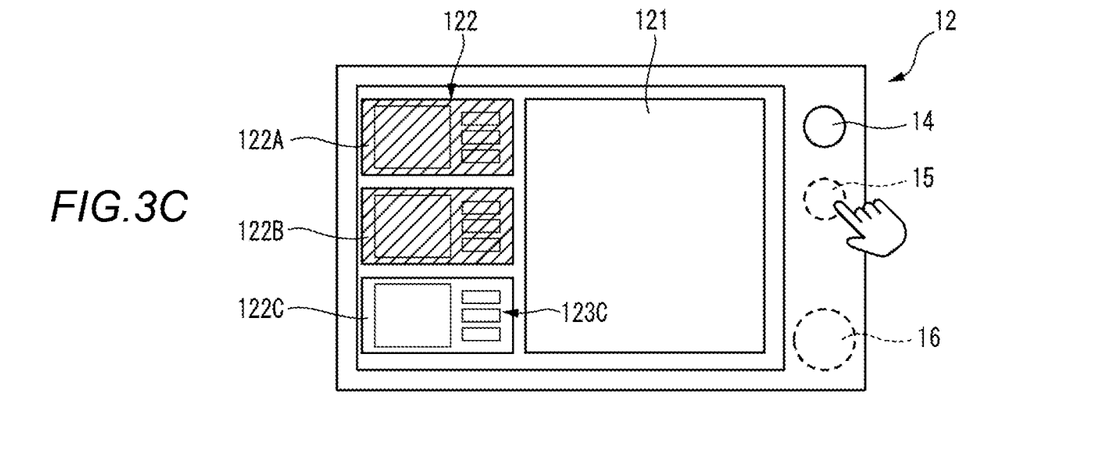

As illustrated in FIG. 3A, the anesthesia machine 1 may include a selection switch 15. The selection switch 15 receives an operation of selecting one of the first region 122A, the second region 122B, and the third region 122C. In the case where the first region 122A is selected in the initial state, when the selection switch 15 is pressed, for example, the state is changed to that where the second region 122B is selected as illustrated in FIG. 3B. When the selection switch 15 is pressed in this state, the state is changed to that where the third region 122C is selected as illustrated in FIG. 3C. When the selection switch 15 is pressed in this state, the state is returned to that where the first region 122A is selected. The selection switch 15 is an example of the selection operation receiving section.

The region in the selected state may be identified in various manners so as to be distinct from the other regions in the non-selected state. As illustrated in FIGS. 3A to 3C, the regions in the non-selected state may be gray out as illustrated in FIGS. 3A to 3C, or the region in the selected state may be highlighted.

The anesthesia machine 1 may be configured so as to inhibit a remote operation input for the syringe pumps 2 through a region in the non-selected state. The operation may be realized as a control process which is performed by, for example, the processor that is disposed in the anesthesia machine 1, and that is not shown. In the case where the first region 122A is in the selected state as illustrated in FIG. 3A, for example, a remote operation for the second syringe pump 2B which is performed on the second remote operation receiving section 123B in the second region 122B that is gray out is disabled. In the same or similar manner, a remote operation for the third syringe pump 2C which is performed on the third remote operation receiving section 123C in the third region 122C that is gray out is disabled.

According to the configuration, in the case where the anesthesia machine 1 and the plurality of syringe pump 2 are used together, it is possible not only to clearly identify the syringe pump 2 which is the operation target, but also to eliminate the possibility that the other syringe pumps 2 which are not the operation target are erroneously operated.

In the example, the selection switch 15 is a hardware switch which is disposed in the vicinity of the display device 12. Alternatively, the selection switch 15 may be provided in the form of a switch image which is displayed on the display device 12, and which can be operated by a touch. In this case, the switch image is another example of the selection operation receiving section. The switching to the syringe pump 2 which is the operation target may be performed in response to a voice input of a predetermined phrase. In this case, a configuration which receives the voice input is a further example of the selection operation receiving section.

As illustrated in FIG. 1, the first syringe pump 2A may include a first operation switch 24A. The first operation switch 24A may be provided in the form of a switch which can input at least one of a push operation and a dial operation. A configuration may be possible where the first syringe pump 2A is caused to perform a predetermined operation, by a predetermined operation which is input through the first operation switch 24A.

In the same or similar manner, the second syringe pump 2B may include a second operation switch 24B. The second operation switch 24B may be provided in the form of a switch which can input at least one of a push operation and a dial operation. A configuration may be possible where the second syringe pump 2B is caused to perform a predetermined operation, by a predetermined operation which is input through the second operation switch 24B.

In the same or similar manner, the third syringe pump 2C may include a third operation switch 24C. The third operation switch 24C may be provided in the form of a switch which can input at least one of a push operation and a dial operation. A configuration may be possible where the third syringe pump 2C is caused to perform a predetermined operation, by a predetermined operation which is input through the third operation switch 24C.

The anesthesia machine 1 may include a common operation switch 16. The common operation switch 16 may be provided in the form of a switch which can input at least one of a push operation and a dial operation. When the first region 122A is selected through the selection switch 15 as illustrated in FIG. 3A, the common operation switch 16 has the same function as the first operation switch 24A which is disposed in the first syringe pump 2A corresponding to the first region 122A.

When an operation is input through the common operation switch 16 in this state, the processor which is disposed in the anesthesia machine 1, and which is not shown selectively transmits a signal corresponding to the operation, to the first syringe pump 2A through the communicating section 13. The first syringe pump 2A which receives the signal performs a movement corresponding to the operation which is input through the common operation switch 16.

When the second region 122B is selected through the selection switch 15 as illustrated in FIG. 3B, the common operation switch 16 has the same function as the second operation switch 24B which is disposed in the second syringe pump 2B corresponding to the second region 122B.

When an operation is input through the common operation switch 16 in this state, the processor which is disposed in the anesthesia machine 1, and which is not shown selectively transmits a signal corresponding to the operation, to the second syringe pump 2B through the communicating section 13. The second syringe pump 2B which receives the signal performs a movement corresponding to the operation which is input through the common operation switch 16.

When the third region 122C is selected through the selection switch 15 as illustrated in FIG. 3C, the common operation switch 16 has the same function as the third operation switch 24C which is disposed in the third syringe pump 2C corresponding to the third region 122C.

When an operation is input through the common operation switch 16 in this state, the processor which is disposed in the anesthesia machine 1, and which is not shown selectively transmits a signal corresponding to the operation, to the third syringe pump 2C through the communicating section 13. The third syringe pump 2C which receives the signal performs a movement corresponding to the operation which is input through the common operation switch 16.

According to the configuration, the plurality of syringe pumps 2 can be remotely controlled while suppressing the number of operation switches which are disposed in the anesthesia machine 1, to the minimum necessary.

The above-described embodiment is a mere example for facilitating understanding of the presently disclosed subject matter. The configuration of the embodiment may be adequately changed or improved without departing from the spirit of the presently disclosed subject matter.

In the above-described embodiment, in the case where the anesthesia machine 1 and the plurality of syringe pumps 2 are communicable with each other, when one of the first region 122A, second region 122B, and third region 122C which are included in the syringe pump information display screen 122 is touch operated, the whole syringe pump information display screen 122 is expanded. In other words, the touch operation causes all of the first region 122A, the second region 122B, and the third region 122C are expanded. Alternatively, a display manner illustrated in FIGS. 4A to 4C may be employed.

Figure 4A:
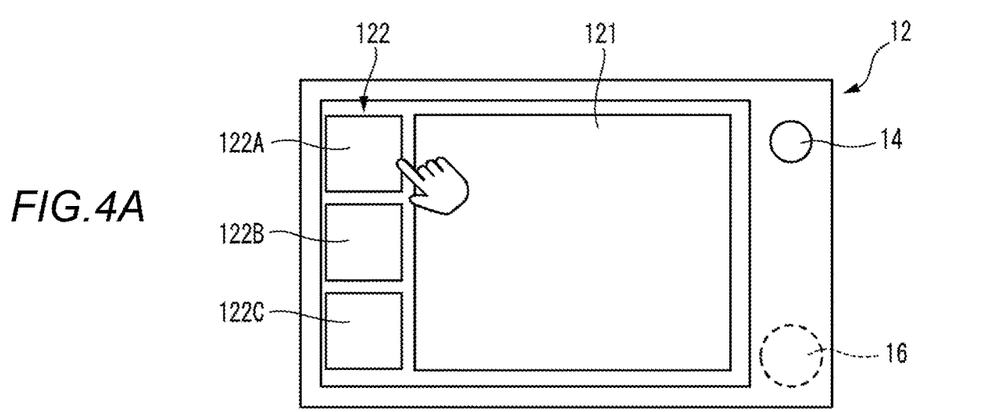
FIGS. 4A to 4C illustrate a further example of the state transition of the display device.
Figure 4B:
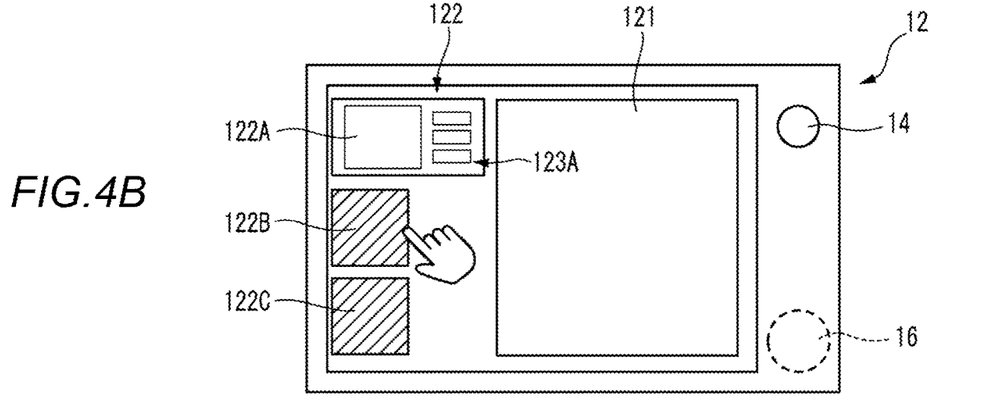

FIG. 4A illustrates a state where, in response to an operation performed on the call switch 14, the syringe pump information display screen 122 including the first region 122A, the second region 122B, and the third region 122C is displayed. When the first region 122A is touch operated in this state, only the first region 122A is expanded so as to contain the first remote operation receiving section 123A as illustrated in FIG. 4B. At this time, the second region 122B and the third region 122C may be gray out.

Figure 4C:
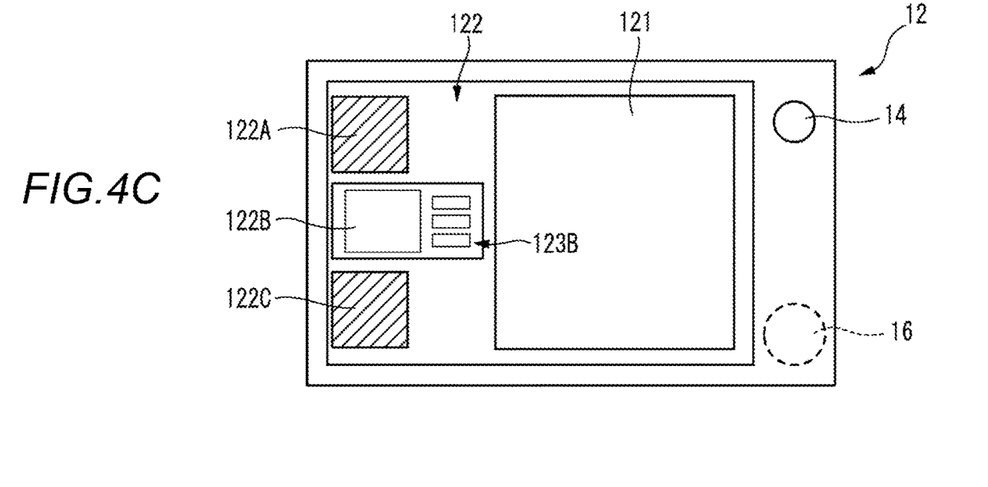

When the second region 122B is touch operated in the state illustrated in of FIG. 4B, only the second region 122B is expanded so as to contain the second remote operation receiving section 123B as illustrated in FIG. 4C. At this time, the first region 122A and the third region 122C may be gray out. The same description can be applied also to the third region 122C.

Also according to the configuration, in the case where the anesthesia machine 1 and the plurality of syringe pump 2 are used together, it is possible not only to clearly identify the syringe pump 2 which is the operation target, but also to eliminate the possibility that the other syringe pumps 2 which are not the operation target are erroneously operated. In this case, each of the first region 122A, the second region 122B, and the third region 122C is a still further example of the selection operation receiving section.

In the above-described embodiment, the case where the one syringe pump 2 is communicable with the anesthesia machine 1, and the other case where the three syringe pumps 2 are communicable with the anesthesia machine 1 have been exemplified. In accordance with the contents of the infusion management which is performed in parallel with anesthetic management using the anesthesia machine 1, however, two or four or more syringe pumps 2 may be communicable with the anesthesia machine 1.

The description of the syringe pump(s) 2 in the embodiment can be applied also to adequate external apparatuses which are used in anesthetic management and infusion management.

What is claimed is:

1. An anesthesia machine comprising:
   a vaporizer configured to administer an anesthetic gas to a patient;
   a communicating section which is communicable with at least one external apparatus;
   a display device which displays a first screen indicating anesthesia information; and
   a first operation receiving section which receives a first input operation,
   wherein when the first operation receiving section receives the first input operation, a second screen indicating operation information of the external apparatus is displayed on the display device, in addition to the first screen, and
   in a case where the at least one external apparatus includes a first external apparatus which is placed in an upper position, and a second external apparatus which is placed in a lower position, a first region indicating operation information of the first external apparatus is displayed in an upper position in the second screen, and a second region indicating operation information of the second external apparatus is displayed in a lower position in the second screen.

2. The anesthesia machine according to claim 1, wherein the second screen is displayed without being superimposed on the first screen, and a size of the first screen is reduced as compared with a size at which the first screen is displayed before the second screen is displayed.

3. The anesthesia machine according to claim 1, further comprising:
   a second operation receiving section which receives a second input operation; and
   a remote operation receiving section which receives an operation of remotely controlling an operation of the external apparatus,
   wherein the second screen which is displayed in response to the first input operation has a first size,
   when the second operation receiving section receives the second input operation, a size of the second screen is changed to a second size which is larger than the first size, and
   the remote operation receiving section is placed in the second screen having the second size.

4. The anesthesia machine according to claim 3, wherein the second size is identical with a size of a display screen of the external apparatus, and
   wherein an information layout in the second screen having the second size is identical with an information layout in the display screen of the external apparatus.

5. The anesthesia machine according to claim 3, wherein the second screen having the first size functions as the second operation receiving section.

6. The anesthesia machine according to claim 3, further comprising:
   a third operation receiving section which receives a third input operation,
   wherein in a case where the third operation receiving section receives the third input operation during when the second screen has the second size, or in a case where a time period when an input operation is not performed on the remote operation receiving section reaches a predetermined value, the size of the second screen returns to the first size.

7. The anesthesia machine according to claim 6, wherein the second screen having the second size functions as the third operation receiving section.

8. The anesthesia machine according to claim 1, wherein the first operation receiving section includes a selection operation receiving section for selecting one of the first region and the second region, and,
   wherein when one of the first region and the second region is selected by the selection operation receiving section, a remote control of the external apparatus corresponding to another one of the first region and the second region is disabled.

9. The anesthesia machine according to claim 8, further comprising:
   a common operation switch,
   wherein when the first region is selected by the selection operation receiving section, the common operation switch has a same function as an operation switch which is disposed in the external apparatus corresponding to the first region, and, when the second region is selected by the selection operation receiving section, the common operation switch has a same function as an operation switch which is disposed in the external apparatus corresponding to the second region.

10. The anesthesia machine according to claim 1, wherein the external apparatus is a syringe pump.

11. The anesthesia machine according to claim 10, wherein
the syringe pump is an administration apparatus for administrating intravenous anesthetic.

12. An anesthesia machine comprising:
a communicating section which is communicable with at least one external apparatus;
a display device which displays a first screen indicating anesthesia information; and
a first operation receiving section which receives a first input operation,
wherein when the first operation receiving section receives the first input operation, a second screen indicating operation information of the external apparatus is displayed on the display device, in addition to the first screen, and
wherein in a case where the at least one external apparatus includes a first external apparatus which is placed in an upper position, and a second external apparatus which is placed in a lower position, a first region indicating operation information of the first external apparatus is displayed in an upper position in the second screen, and a second region indicating operation information of the second external apparatus is displayed in a lower position in the second screen.

13. The anesthesia machine according to claim 12, wherein
the first operation receiving section includes a selection operation receiving section for selecting one of the first region and the second region, and,
wherein when one of the first region and the second region is selected by the selection operation receiving section, a remote control of the external apparatus corresponding to another one of the first region and the second region is disabled.

14. The anesthesia machine according to claim 13, further comprising:
a common operation switch,
wherein when the first region is selected by the selection operation receiving section, the common operation switch has a same function as an operation switch which is disposed in the external apparatus corresponding to the first region, and,
when the second region is selected by the selection operation receiving section, the common operation switch has a same function as an operation switch which is disposed in the external apparatus corresponding to the second region.

* * * * *